United States Patent [19]

Krause et al.

[11] Patent Number: 4,486,357

[45] Date of Patent: Dec. 4, 1984

[54] PROCESS FOR MAKING VINYLPHOSPHONIC ACID OR VINYLPYROPHOSPHONIC ACID

[75] Inventors: Werner Krause, Hürth; Werner Pieper, Erftstadt, both of Fed. Rep. of Germany

[73] Assignee: Hoechst Aktiengesellschaft, Fed. Rep. of Germany

[21] Appl. No.: 580,774

[22] Filed: Feb. 21, 1984

Related U.S. Application Data

[63] Continuation of Ser. No. 390,190, Jun. 21, 1982, abandoned.

[30] Foreign Application Priority Data

Jun. 27, 1981 [DE] Fed. Rep. of Germany ....... 3125329

[51] Int. Cl.$^3$ ................................................. C07F 9/38
[52] U.S. Cl. ........................... 260/502.4 R; 260/545 P
[58] Field of Search ...................... 260/502.4 R, 545 P

[56] References Cited

U.S. PATENT DOCUMENTS

| | | | |
|---|---|---|---|
| 2,230,371 | 2/1941 | Bolton | 260/502.4 R |
| 2,254,124 | 8/1941 | Stevens et al. | 260/502.4 R |
| 2,279,501 | 4/1942 | Dickey et al. | 260/502.4 R |
| 2,365,466 | 12/1944 | Hamilton | 260/502.4 R |
| 2,686,803 | 8/1954 | Stayner | 260/502.4 R |
| 2,693,482 | 11/1954 | Stayner | 260/502.4 R |
| 2,694,684 | 11/1954 | Rogers et al. | 260/502.4 R |

OTHER PUBLICATIONS

Houben-Weyl, *Methoden der Organischen Chemie*, 4th Edition, vol. XII/I, Part 1 ("Organic Phosphorus Compounds"), Georg Thieme Verlag., Stuttgart, 1963, pp. 363, 364, 374.

*Primary Examiner*—J. E. Evans
*Attorney, Agent, or Firm*—Connolly & Hutz

[57] ABSTRACT

The disclosure relates to process for making derivatives of vinylphosphonic acid or vinylpyrophosphonic acid. To this end, a ketone is reacted with tetraphosphorus hexoxide in the presence of catalytic proportions of a proton-yielding substance. In the event of the products desired to be produced being vinylphosphonic acid derivatives, the vinylpyrophosphonic acid derivatives first obtained are hydrolyzed with an equivalent quantity of water.

13 Claims, No Drawings

PROCESS FOR MAKING VINYLPHOSPHONIC ACID OR VINYLPYROPHOSPHONIC ACID

This application is a continuation of Ser. No. 390,190 filed June 21, 1982, now abandoned.

The present invention relates to a process for making derivatives of vinylphosphonic acid or vinylpyrophosphonic acid.

Vinylphosphonic acid, vinylpyrophosphonic acid and their derivatives are compounds of commercial interest as they can be polymerized to compounds of high molecular weight or made together with further polymerizable vinyl compounds into copolymers.

Heretofore, vinylphosphonic acids have been made by reacting ketones with $PCl_3$. The process carried out in a plurality of operational steps involving the formation of various intermediate products (see Rogers et al, U.S. Pat. No. 2,694,684, issued Nov. 16, 1954, column 2, lines 1–65) and entails considerable adverse effects and corrosiveness originating from chlorine which is separated in the form of hydrogen chloride or acetyl chloride.

The present invention now provides a process which is easy to carry out and avoids the adverse effects just referred to and which comprises: reacting a ketone with tetraphosphorus hexoxide ($P_4O_6$) in the presence of catalytic proportions of a proton-yielding substance at elevated temperatures and, in the event of the products desired to be produced being vinylphosphonic acid derivatives, hydrolyzing the vinylpyrophosphonic acid derivatives first obtained with an equivalent quantity of water.

The ketone and $P_4O_6$ should preferably be reacted in a molar ratio of at least 4:1.

It is good practice to use the proton-yielding substance in proportions of a least 0.0001 weight %, preferably 0.01 to 1 weight %, based on $P_4O_6$, and to effect the reaction at temperatures of 40° to 150° C.

The proton-yielding substances should be selected, for example, from the group consisting of water, alcohols, amines, hydrochloric acid, sulfuric acid, phosphoric acid, phosphorous acid, phosphonic acids or carboxylic acids.

A particularly advantageous feature provides for the respective final product to be used as the proton-yielding substance which permits the reaction to be carried out in the absence of foreign substances.

The useful ketones comprise compounds of the following general formula:

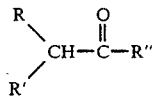

in which R and R' being identical or different stand for hydrogen or a halogen-substituted or unsubstituted alkyl group, aryl group, alkaryl group or aralkyl group having from 1 to 18 carbon atoms, and R" stands for an alkyl group, aryl group, alkaryl group or aralkyl group having from 1 to 18 carbon atoms.

The process should preferably be effected by metering $P_4O_6$ into the ketone which may optionally be diluted with an inert organic solvent. Needless to say, $P_4O_6$ may also be diluted with an inert organic solvent, if desired. In order to initiate the reaction, it is necessary for the ketone to contain a catalytic proportion of a substance capable of readily yielding protons and reacting spontaneously with $P_4O_6$ with break-up of a P—O—P—bond.

The $P_4O_6$ should preferably be added continuously at elevated temperatures, especially within the range 40° to 150° C., within which $P_4O_6$ undergoes complete exothermal reaction. During the reaction, it is commonly not necessary to use additional heat as the reaction enthalpy normally permits the selected temperature to be maintained so that it is possible for the temperature to be controlled by means of the $P_4O_6$ introduction velocity.

In those cases in which highly reactive ketones, e.g. acetophenone, are concerned, the reaction directly results in the formation of vinylpyrophosphonic acid derivatives, which are either isolated or such or, after addition of the necessary stoichiometric quantities of water, are made into corresponding vinylphosphonic acid derivatives.

In all other cases, the polymeric crude product first obtained by reacting the ketone with $P_4O_6$ is subjected to thermal after-treatment. To this end, the crude product is heated over a period of 10 to 60 minutes to temperatures lying between reaction temperature and 250° C. The minimum temperature to be used depends on the reactivity of the particular ketone used. In this manner, crude vinylpyrophosphonic acid derivatives are obtained which are converted to vinylphosphonic acid derivatives by addition of the necessary calculated quantity of water.

It is also possible for the crude product to be reacted in an autoclave with an excess of water at elevated temperatures and under elevated pressure with direct formation of vinylphosphonic acid derivatives.

As illustrated in the following Examples, the present process is a new route to phosphonic acid compounds which are readily obtainable in high yields by reacting tetraphosphorus hexoxide with ketones.

This reaction has not been described heretofore as far as we are aware. No reaction can indeed be found to occur upon the addition of one reactant to the other. In view of this, it is all the more an unexpected result for the artisan that an exothermal reaction is initiated in the presence of catalytic proportions of proton-yielding substances.

EXAMPLE 1

61.2 g acetophenone and 1 g 1-phenylvinyl-1-phosphonic acid were placed under nitrogen in a multinecked flask provided with a stirrer, reflux condenser, dropping funnel and internal diameter, and 27.5 g tetraphosphorus hexoxide dissolved in 50 ml toluene was added dropwise at 100° C. so that the reaction temperature remained constant without supply of additional heat. After the reaction was complete, the solution was allowed to cool and pure 1-phenyl-vinylpyrophosphonic acid was obtained by crystallization. The yield was 55 g or 61%. The melting point was 113° to 118° C.

In order to produce the corresponding phosphonic acid, the crude reaction solution was admixed at 40° to 50° C. with 5 ml water and diluted with a further 130 ml toluene. After cooling to room temperature, precipitated 1-phenyl-vinyl-1-phosphonic acid was removed by suction filtration and dried. The yield was 78 g or 85% and the melting point was 108° C.

The filtrate which still contained desirable product was used in the next batch. By recycling the filtrate, it was possible to increase the yield to about 90%.

EXAMPLE 2

50 g p-bromacetophenone and 0.13 ml water were placed in an apparatus as described in Example 1 and a solution of 13.8 g tetraphosphorus hexoxide in 25 ml toluene was added dropwise at 100° C. Next, the whole was cooled down to 40°–50° C. and resulting pyrophosphonic acid was hydrolyzed by adding 2.5 ml water thereto. After cooling to room temperature, 1-p-bromophenylvinyl-1-phosphonic acid was filtered off and dried. The yield was 48.5 g or 73% and the melting point was 157° C.

By recycling the filtrate, it was possible to increase the yield to more than 80%.

EXAMPLE 3

67 g propiophenone and 0.25 ml water was placed in an apparatus as described in Example 1 and a solution of 27.5 g tetraphosphorus hexoxide in 50 ml 1,2-dichlorobenzene was added dropwise at 140° to 145° C. After a post-reaction period of 15 minutes at 145° C., the whole was allowed to cool down to 40° to 50° C. and hydrolyzed by the addition of 5 ml water. Next, the whole was diluted with 140 ml 1,2-dichlorobenzene and inoculated with a minor proportion of 1-phenyl-propene-1-phosphonic acid. After cooling to room temperature, crystalline matter was filtered off, washed with hexane and dried. The yield was 87 g or 88% and the melting point was 120° to 127° C. By recycling the filtrate, it was possible to increase the yield to more than 90%.

The final product was a cis-trans isomeric mixture of 1-phenylpropene-1-phosphonic acid. Nuclear resonance investigations indicated a cis-trans ratio of about 2:3.

EXAMPLE 4

250 ml toluene, 196 g (2 moles) cyclohexanone and 0.5 ml water were placed in an apparatus as described in Example 1, and 110 g (0.5 mol) tetraphosphorus hexoxide was added dropwise while cooling with a water bath so that the reaction temperature did not exceed 80° C. The yellow orange colored medium viscous liquid which was not allowed to undergo any significant post-reaction, was admixed dropwise with 250 ml water. A resin commenced separating as early as upon the introduction of the first drops of water. Next, the resin was boiled for 3 hours during which its viscosity decreased while its watersolubility increased. Two phases were obtained of which the lower aqueous phase was separated and stripped with steam so as to expel residual dissolved toluene. After about 1 hour, a clear yellow solution was obtained. It was heated for 2 hours in an autoclave to 250° C. Matter hydrolyzed under pressure was freed from water under vacuum in a rotary evaporator and 324 g of a yellow viscous crude product was obtained which slowly crystallized completely. $^{31}$P-NMR-spectroscopy indicated that 75% of the crude product was cyclohexene-1-phosphonic acid, 9% was phosphorous acid and 15% was phosphoric acid, the percentages being based on the phosphorus used. After recrystallization from glacial acetic acid, 230 g (1.42 mols) cyclohexene-1-phosphonic acid was obtained. It had a melting point of 128° C. and was obtained in a yield of 71% of the theoretical.

EXAMPLE 5

800 ml acetone and 0.5 g propene-2-phosphonic acid were placed in an apparatus as described in Example 1 and heated to 50° C. Next, 88 g (0.4 mol) tetraphosphorus hexoxide was added dropwise so that the acetone boiled gently under reflux. White amorphous solid material was obtained. It was stirred for about a further 1 h without supply of additional heat and then admixed dropwise with 14.4 g (0.8 mol) water, the reaction temperature increasing once again to more than 50° C. The whole was stirred for 30 minutes without supply of heat and the white solid material was removed by suction filtration and dried to constant weight. 192 g of this material was dissolved in 300 ml hot water and the solution was heated for 2.5 hours to 210° to 240° C. in an autoclave. Next, water was removed under vacuum and 190 g of a viscous colorless liquid was obtained. It was heated for 15 minutes to 200° C. $^{31}$P-NMR-spectroscopy indicated 64% of the product was propene-2-phosphonic acid.

EXAMPLE 6

As described in Example 5, the primary product prepared from tetraphosphorus hexoxide and acetone was partially hydrolyzed and a 50% aqueous solution thereof was introduced dropwise into a quartz tube packed with Raschig rings and heated to 250° C. Nitrogen was passed through the tube countercurrently with respect to the primary product. Water escaped from the system via a column head, and thermolyzed product was taken from the lower end of the quartz tube and placed in a receiver. $^{31}$P-NMR-spectroscopy indicated 57% of the thermolyzed product was propene-2-phosphonic acid, the percentge being based on the phosphorus used.

EXAMPLE 7

62.5 g methylisobutylketone and 0.25 ml water were placed in an apparatus as described in Example 1 and 27.5 g P$_4$O$_6$ was added dropwise at 100° C. Next, the mixture was heated for 30 minutes to 200° C. After cooling down to 50° C., the pyrophosphonic acid mixture so obtained was hydrolyzed by adding 5 ml water thereto. A viscous slightly yellowish oil was obtained which crystallized completely within a few days. Nuclear resonance investigations indicated that the product consisted to an extent of 93% of substituted pentenephosphonic acids, which were distributed as follows:
11% 4-methyl-2-pentene-2-phosphonic acid (cis)
66% 4-methyl-2-pentene-2-phosphonic acid (trans)
23% 4-methyl-1-pentene-2-phosphonic acid.

We claim:
1. A process for making phosphonic or pyrophosphonic acids from ketones, comprising:
reacting a ketone of the formula

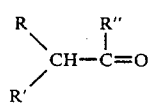

in which
R and R' are identical or different and stand for hydrogen or a halogen-substituted or unsubstituted alkyl group, aryl group, alkaryl group or aralkyl group having from 1 to 18 carbon atoms, and R'' stands for an alkyl group, aryl group, alkaryl group, or aralkyl group having from 1 to 18 carbon atoms, with tetraphosphorus hexoxide (P$_4$O$_6$) in the presence of at least 0.0001 weight %, based on the tetraphosphorus hexoxide, of a proton donor at elevated temperatures, and obtaining a phosphonic or pyrophosphonic acid reaction product having a substituted vinyl group, the said substituted vinyl group being substituted by R" on one of the carbons of the vinyl group, and, if R and R' are not hydrogen, by R and R', on the other carbon of the vinyl group.

2. A process according to claim 1, wherein the vinylpyrophosphonic acid reaction product is isolated as such.

3. A process according to claim 1, wherein a vinylpyrophosphonic acid product is obtained as the reaction product and is hydrolyzed to the corresponding vinylphosphonic acid, which is recovered as the final product.

4. A process according to claim 3, comprising the step of:

reacting a ketone of the formula

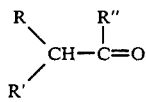

with phosphorus hexoxide in the presence of at least 0.0001 weight % of a proton donor at elevated temperatures thereby obtaining an R, R', and R"-substituted pyrophosphonic acid reaction product, R, R' and R" having the previously defined meanings, and hydrolyzing said pyrophosphonic acid product with an equivalent of water to obtain the corresponding vinylphosphonic acid,

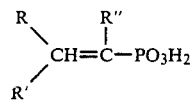

R, R', and R" having the previously defined meanings, and recovering said corresponding vinylphosphonic acid.

5. A process according to claim 4 wherein in said ketone, R is H, R' is H or methyl, and R" is an alkyl or aryl group.

6. A process for making cyclohexene-1-phosphonic acid, comprising:

reacting cyclohexanone with tetraphosphorus hexoxide in the presence of at least 0.0001 weight %, based on the tetraphosphorus hexoxide, of a proton donor, at elevated temperatures, adding water and hydrolyzing the resulting mixture, and isolating cyclohexane-1-phosphonic acid.

7. The process according to claim 1, wherein the P$_4$O$_6$ and ketone, are reacted in a molar ratio of at least 4:1.

8. The process according to claim 1, wherein the proton donor is used in proportions of 0.1 to 1.0 weight %, based on P$_4$O$_6$.

9. The process according to claim 1, wherein the reaction is effected at temperatures of 40° to 150° C.

10. The process according to claim 1, wherein the proton donor is a member selected from water, alcohols, amines, hydrochloric acid, sulfuric acid, phosphoric acid, phosphorous acid, phosphonic acids or carboxylic acids.

11. The process according to claim 10 whrein the proton donor is the vinylphosphonic acid or vinylpyrophosphoric acid intended as the product of the reaction between the ketone and P$_4$O$_6$.

12. The process according to claim 1, wherein the reaction product is heat-treated at temperatures between the reaction temperature and 250° C.

13. The process as claimed in claim 1, wherein the reaction product is subjected to hydrolysis under pressure at temperatures between the reaction temperature and 250° C.

* * * * *